United States Patent
Corlett et al.

(12)

(10) Patent No.: US 6,482,325 B1
(45) Date of Patent: Nov. 19, 2002

(54) APPARATUS AND PROCESS FOR SEPARATION AND RECOVERY OF LIQUID AND SLURRY ABRASIVES USED FOR POLISHING

(75) Inventors: Gary L. Corlett, Hollister, CA (US); Edward T. Ferri, Jr., Gilroy, CA (US); J. Tobin Geatz, Wilmington, NC (US)

(73) Assignee: Linica Group, Ltd., Hollister, CA (US)

( * ) Notice: Subject to any disclaimer, the term of this patent is extended or adjusted under 35 U.S.C. 154(b) by 0 days.

(21) Appl. No.: 09/813,037

(22) Filed: Mar. 19, 2001

Related U.S. Application Data (60) Division of application No. 09/299,697, filed on Apr. 26, 1999, now Pat. No. 6,379,538, which is a continuation-in-part of application No. 08/870,082, filed on Jun. 5, 1997, now Pat. No. 5,928,492, and a continuation-in-part of application No. 09/099,280, filed on Jun. 18, 1998, now abandoned.

(51) Int. Cl.$^7$ .................................................. C02F 1/42
(52) U.S. Cl. ....................... 210/662; 210/739; 210/742; 210/743; 210/805; 137/93; 134/10; 451/60; 451/88
(58) Field of Search ..................... 210/85, 96.1, 143, 210/167, 257.1, 258, 660, 739, 742, 743, 662, 96.2, 97, 418, 745, 746, 805; 451/60, 88, 446; 134/10, 109–111, 902; 141/279; 137/2, 93

(56) References Cited

U.S. PATENT DOCUMENTS

| | | |
|---|---|---|
| 1,558,382 A | 10/1925 | Marx |
| 1,962,463 A | 6/1934 | Renfrew |
| 3,253,711 A | 5/1966 | Young |
| 3,493,120 A | 2/1970 | Milner |
| 3,556,967 A | 1/1971 | Anderson |

(List continued on next page.)

FOREIGN PATENT DOCUMENTS

| | | |
|---|---|---|
| DE | 24 19 479 A1 | 11/1975 |
| DE | 3328312 A1 | 2/1985 |
| DE | 40 06 689 A1 | 1/1991 |

(List continued on next page.)

OTHER PUBLICATIONS

PCT/US00/10581 International Search Report, published Aug. 21, 2000.

*Primary Examiner*—Joseph W. Drodge
(74) *Attorney, Agent, or Firm*—Fulwider Patton Lee & Utecht, LLP (57) ABSTRACT

Abrasive components and clear fluids are separated from an aqueous chemical mechanical slurry used for planarization of semiconductor materials, to permit the reuse of the clear liquid effluent in non-process applications as well as for gray water for irrigation, process cooling water, or as make-up water for a reverse osmosis system, or safe disposal in the industrial waste stream, as desired. A solids detection device determines the concentration of abrasive solids in the aqueous waste effluent stream, and a diverter valve receives and diverts the entire aqueous waste effluent stream to at least one reuse water collection tank when the abrasive solids concentration is below a desired threshold, and diverts the entire aqueous waste effluent stream to at least one concentrate water collection tank when the abrasive solids concentration is greater than or equal to the threshold. With the additional use of ion exchange, the resulting water stream can be reused in high purity water applications.

13 Claims, 7 Drawing Sheets

U.S. PATENT DOCUMENTS

| | | |
|---|---|---|
| 3,741,394 A | 6/1973 | Defenbaugh |
| 3,788,473 A | 1/1974 | King |
| 3,834,418 A | 9/1974 | Clancy |
| 3,970,536 A | 7/1976 | Shettel |
| 3,971,412 A | 7/1976 | Wierzbicki |
| 3,973,987 A | 8/1976 | Hewitt et al. |
| 4,017,390 A | 4/1977 | Vicard |
| 4,031,006 A | 6/1977 | Ramirez et al. |
| 4,064,893 A | 12/1977 | Pitt |
| 4,069,157 A | 1/1978 | Hoover et al. |
| 4,231,399 A | 11/1980 | Pauliukonis |
| 4,295,946 A | 10/1981 | Nazarian et al. |
| 4,388,080 A | 6/1983 | Kapur et al. |
| 4,414,091 A | 11/1983 | Axenko et al. |
| 4,475,897 A | 10/1984 | Bradtmöller |
| 4,482,459 A | 11/1984 | Shiver |
| 4,535,821 A | 8/1985 | Anderson |
| 4,588,492 A | 5/1986 | Bier |
| 4,598,736 A | 7/1986 | Chorkey |
| 4,642,160 A | 2/1987 | Yoshisato et al. |
| 4,683,042 A | 7/1987 | Scott |
| 4,900,421 A | 2/1990 | Grutzner et al. |
| 4,917,123 A | 4/1990 | McConnell et al. |
| 5,006,248 A | 4/1991 | Anderson et al. |
| 5,017,286 A | 5/1991 | Heiligman |
| 5,030,351 A | 7/1991 | Burggraaf et al. |
| 5,073,268 A | 12/1991 | Saito et al. |
| 5,082,541 A | 1/1992 | Watson |
| 5,104,546 A | 4/1992 | Filson et al. |
| 5,128,043 A | 7/1992 | Wildermuth |
| 5,200,050 A | 4/1993 | Ivory et al. |
| 5,242,595 A | 9/1993 | Morgart et al. |
| 5,250,184 A | 10/1993 | Maier |
| 5,338,459 A | 8/1994 | Hirose |
| 5,372,725 A | 12/1994 | Halff et al. |
| 5,425,883 A | 6/1995 | Reid et al. |
| 5,518,624 A | 5/1996 | Filson et al. |
| 5,664,990 A * | 9/1997 | Adams et al. ............... 451/60 |
| 5,681,457 A | 10/1997 | Mahoney |
| 5,681,482 A | 10/1997 | Reber |
| 5,772,900 A | 6/1998 | Yorita et al. |
| 5,855,792 A | 1/1999 | Adams et al. |
| 6,178,975 B1 | 1/2001 | Aoki |
| 6,379,538 B1 * | 4/2002 | Corlett et al. ............. 210/96.1 |

FOREIGN PATENT DOCUMENTS

| | | |
|---|---|---|
| DE | 40 05 627 A1 | 8/1991 |
| DE | 195 32 802 C1 | 5/1997 |
| EP | 0 048 603 A1 | 3/1982 |
| EP | 761603 | 3/1997 |
| FR | 1 593 489 | 5/1970 |
| FR | 2655657 | 6/1991 |
| GB | 646236 | 11/1950 |
| GB | 2 081 848 A | 2/1982 |
| GB | 2 252 122 A | 7/1992 |
| RU | 197712 | 12/1997 |
| WO | WO 81/01525 | 6/1981 |
| WO | WO 94/11728 | 5/1994 |
| WO | WO 98/49102 | 11/1998 |
| WO | WO 99-65592 | 12/1999 |

* cited by examiner

APPARATUS AND PROCESS FOR SEPARATION AND RECOVERY OF LIQUID AND SLURRY ABRASIVES USED FOR POLISHING

RELATED APPLICATIONS

This is a divisional of Ser. No. 09/299,697, filed Apr. 26, 1999, now U.S. Pat. No. 6,379,538, which is a continuation-in-part of Ser. No. 08/870,082, filed Jun. 5, 1997, now U.S. Pat. No. 5,928,492, and a continuation-in-part of Ser. No. 09/099,280, filed Jun. 18, 1998, now abandoned, all of which are incorporated herein by reference.

BACKGROUND OF THE INVENTION

1. Field of the Invention

This invention relates generally to chemical mechanical processing of semiconductor wafers, and more particularly concerns a method and apparatus for recovery of components of an aqueous chemical mechanical abrasive slurry containing finely divided, suspended particles following their use in processing of semiconductor wafers. The invention herein relates specifically to an apparatus for diverting flow in a waste stream into clean and turbid components.

2. Description of Related Art

Semiconductor components are commonly manufactured by layering electrically conductive and dielectric materials to achieve appropriate electrical characteristics for fabrication of multiple electrical components such as resistors, capacitors and transistors. Many of these discrete devices are incorporated into integrated circuits for use in creating microprocessors, memory devices, logic circuits, and the like. Many integrated circuits can be produced on semiconductor wafers by layering of dielectric and electrically conductive materials to create multiple semiconductor devices in a relatively small area.

The density of electrical components and interconnect wiring on such semiconductor devices has continually increased as trace line widths on such semiconductor devices have narrowed. At one time, for example, trace line widths on such devices typically ranged from 1 $\mu$m to 4 $\mu$m. However, in recent years, the industry has made significant advances in reducing trace line widths used in creation of integrated circuits to less than 1 $\mu$m. Currently, trace line widths of 0.18 $\mu$m to 0.25 $\mu$m are common, and research is being done to achieve trace line widths of from 0.15 $\mu$m to 0.18 $\mu$m. In addition, the demand for increased memory and computing power has driven the limits on the number of semiconductor devices per integrated circuit that are achievable ever higher, resulting in an increase in the number of layers applied to semiconductor wafers, while the typical size of the integrated circuits continues to decrease. The combination of narrower trace line widths, increased layers of materials and higher densities of semiconductor devices per integrated circuit has made such devices increasingly susceptible to failure due to inconsistencies on semiconductor wafer surfaces, and it has become increasingly important that such semiconductor wafers have surfaces and dielectric layers that are uniformly smooth.

Methods for chemical mechanical planarization (CMP) have been developed to polish the surface of semiconductor wafers, and typically involve rotating the wafer on a polishing pad, applying pressure through a rotating chuck, and supplying an aqueous chemical slurry containing an abrasive polishing agent to the polishing pad for both surfactant and abrasive processing. Abrasive agents that can be used in the chemical mechanical slurry include particles of fumed or colloidal silica, ceria, and alumina. The chemical mechanical slurry can also include stabilizer or oxidizer agents. Silica is typically mixed with a stabilizer such as potassium hydroxide or ammonium hydroxide, and is commonly used to polish dielectric or oxide layers on the semiconductor wafer. Ceria and Alumina are commonly mixed with an oxidizer agent such as ferric nitrate or hydrogen peroxide, and are typically used to polish metal layers, such as tungsten, copper and aluminum, for example.

The slurry and material removed from the various layers of the semiconductor wafer form a waste stream that is commonly disposed of as industrial waste. The abrasive components constitute approximately 8% to 15% by weight of the process CMP slurry, with the remainder constituting other chemical agents such as stabilizer or oxidizer agents, and water. The raw waste stream is typically diluted with other process deionized (DI) water in the CMP polishers to yield a final solids concentration of 0.2% to 1.0% by weight in the waste stream. However, the disposal of dissolved or suspended solids in the industrial waste stream has become a relevant issue due to strict local, state and federal regulations, and it would thus be desirable to provide a process and apparatus to remove abrasive components from the waste stream for possible removal of heavy metal components for separate disposal.

Since, for a significant amount of time, the waste stream contains only DI water containing little, in any, contaminants; it would also be desirable to recover as much of this water as possible to permit reuse of the water in the chemical mechanical planarization process. Ideally, this reclaim process would occur at the polisher tool in order to effectively reuse the DI water and simultaneously save costs. While conventional filtration technology exists for point-of-use filtration, this technology is not suited for the high probability of suspended matter in the waste stream. With conventional filtration, all effluent flow is into the filter at a perpendicular angle to the membrane element. The particles embed in the membrane media and the filter subsequently clogs. This causes high downtime and related operating costs.

Alternatives to point-of-use filtration include central plant treatments such as pH neutralization and the addition of flocculating or settling agents in conjunction with filter presses; ultrafiltration or reverse osmosis filtration systems. These systems represent a prohibitively costly system for users with just several polishing tools and continuing high operation costs. Further, these systems are gravity drain based. Because of the nature of the suspended solids in the slurry effluent, and the common practice of combining waste streams at a central point prior to treatment, any clear waste collected is sufficiently mixed with particulate bearing fluid as to require treatment of the entire waste stream. It is therefore desirable to have a process which recovers the usable water from the process and eliminates the primary suspended particles problem near the point of origination of the waste stream, yet is flexible enough to meet slurry specific problems. It is also desirable to have a process that is scalable from pilot production to full scale manufacturing. The present invention meets these needs.

SUMMARY OF THE INVENTION

Briefly, and in general terms, the present invention provides for the separation of abrasive components and clear fluids from an aqueous chemical mechanical slurry used for planarization of semiconductor materials, to permit the reuse of the clear liquid effluent in non-process applications as well as for gray water for irrigation, process cooling water, or as make-up water for a reverse osmosis system, or safe disposal in the industrial waste stream, as desired. With the additional use of continuous ion exchange, the resulting water stream can be reused in high purity water applications.

The invention accordingly provides for a method and apparatus for recovering clear liquid from an aqueous slurry waste stream and for concentrating particles of abrasive materials from the same aqueous solution. In one presently preferred embodiment, the apparatus comprises a solids detection device for detecting the concentration of abrasive solids in the aqueous waste stream. The solids detection device preferably receives raw waste including the aqueous slurry containing abrasive particles and materials removed from planarization of semiconductor materials from the polishing tool, and is preferably located in a location of close proximity to the polishing tool. The solids detection device may optionally also detect other materials, and may also optionally measure incoming flow, effluent conductivity, temperature, turbidity, and/or pH. In a presently preferred embodiment, the sensor is of the type which detects solids concentration using light scattering turbidity measurements, combined with conductivity and temperature measurements. A diverter valve receiving the effluent flow from the solids detection device is also provided for diverting the entire effluent stream including the aqueous slurry containing abrasive particles and materials removed from planarization of semiconductor materials to at least one reuse water collection tank when the abrasive solids concentration is below a desired threshold, and to at least one concentrate water collection tank when the abrasive solids concentration is greater than or equal to the desired threshold.

In a first presently preferred embodiment, the diverter valve comprises a displaceable conduit, and a piston cylinder connected to the displaceable conduit by a collar. The piston cylinder is controlled by the solids detection apparatus, and the displaceable conduit is moveable between first and second positions, such that when the solids concentration is above a desired threshold, the solids detection apparatus causes the piston cylinder to move to the first position, directing the displaceable conduit outlet to the one or several concentrate water collection tanks, and when the solids concentration is below a desired threshold, the solids detection apparatus activates the piston cylinder to move to the second position, in which the displaceable conduit diverts the clear liquid of the effluent to the one or several reuse water collection tanks. In a preferred aspect of the invention, the displaceable conduit comprises a flexible hose.

In another presently preferred embodiment, the diverter valve comprises a valve housing having an inlet, a first outlet for diverting flow to the one or several concentrate water collection tanks, and a second outlet for diverting flow to the one or several reuse water collection tanks. A solenoid is connected for control by the solids detection apparatus, and is connected to a valve piston movable between first and second positions, the valve piston having a first channel for diverting flow to the first outlet in the first valve piston position, and having a second channel for diverting flow to the second outlet in the second valve piston position. In a presently preferred modification, the diverter valve can further comprise a safety valve connected to the inlet of the diverter valve.

In another presently preferred embodiment, the diverter valve comprises a valve housing having an inlet, a first outlet for diverting flow to the one or several concentrate water collection tanks, and a second outlet for diverting flow to the one or several reuse water collection tanks. A solenoid is connected for control by the solids detection apparatus, and is connected to a valve piston movable by the solenoid between first and second positions, the valve piston blocking flow to the second outlet for diverting flow to the first outlet in the first valve piston position, and blocking flow to the first outlet for diverting flow to the second outlet in the second valve piston position.

In a presently preferred aspect of the apparatus of the invention, a pump can be provided for directing the reuse water for reuse as non-process equipment rinse water, or as process water in non-critical rinsing applications in the polishing tool, or for other applications. Optionally, the reuse water can be subjected to an ion exchanger for an ion exchange treatment prior to reuse in process applications. In another preferred aspect, a source of deionized water may be provided, for directing deionized water to the polisher, such as when adequate reclaimed water is not available from collection tanks.

In a presently preferred embodiment a pump can also be provided for directing the concentrate water from the concentrate water collection tanks to a concentrator apparatus which further separates the clear liquid component from the abrasive solids and concentrates the abrasive solids for disposal. In one preferred aspect, means are provided for directing clear liquid from the concentrator apparatus for reuse, or to an industrial waste treatment system for disposal.

In the method of the invention, an aqueous slurry waste stream which, on an irregular basis, contains an abrasive component, is introduced into a particle detection device which uses one of several technologies to detect the presence of abrasive particles. The detection device may use optical, ultrasonic or other similar detection techniques to measure the density of the abrasive solids in the effluent stream. Based on the measurement made by the detection device, when solids concentrations below a desired threshold are indicated, the effluent stream is diverted by way of a diverter valve to one or several small reuse water collection tanks. The collected liquid is pumped back to the polisher through an apparatus which provides non-process water to the polisher for reuse as rinse water. Further, when used in conjunction with ion exchange technologies, including resin beds and continuous ion exchange, or elutriation to achieve high quality deionized water, the water stream may be diverted to high purity, process water applications. Alternatively, when a solids concentration over the desired threshold is detected, the entire waste stream is diverted by way of a diverter valve to one or several small concentrate water collection tanks. The collected concentrate is motivated under pressure to another device for further concentration and processing. This apparatus is capable of concentrating the polisher waste stream from as little as 0.2% solids by weight to as high as 4% solids by weight without additional filtration or waste treatment means.

These and other aspects and advantages of the invention will become apparent from the following detailed description and the accompanying drawings, which illustrate by way of example the features of the invention.

DETAILED DESCRIPTION OF THE PREFERRED EMBODIMENTS

As the density of electrical components and wiring in semiconductor devices have increased, such devices have become increasingly susceptible to failure due to surface irregularities on semiconductor wafers. Conventional methods utilized in the industry for chemical mechanical planarization of the surface of semiconductor wafers to address this problem commonly result in a wasteful disposal of the abrasive agents and water in the slurry used for polishing the various layers of the semiconductor wafers.

Figure 1:
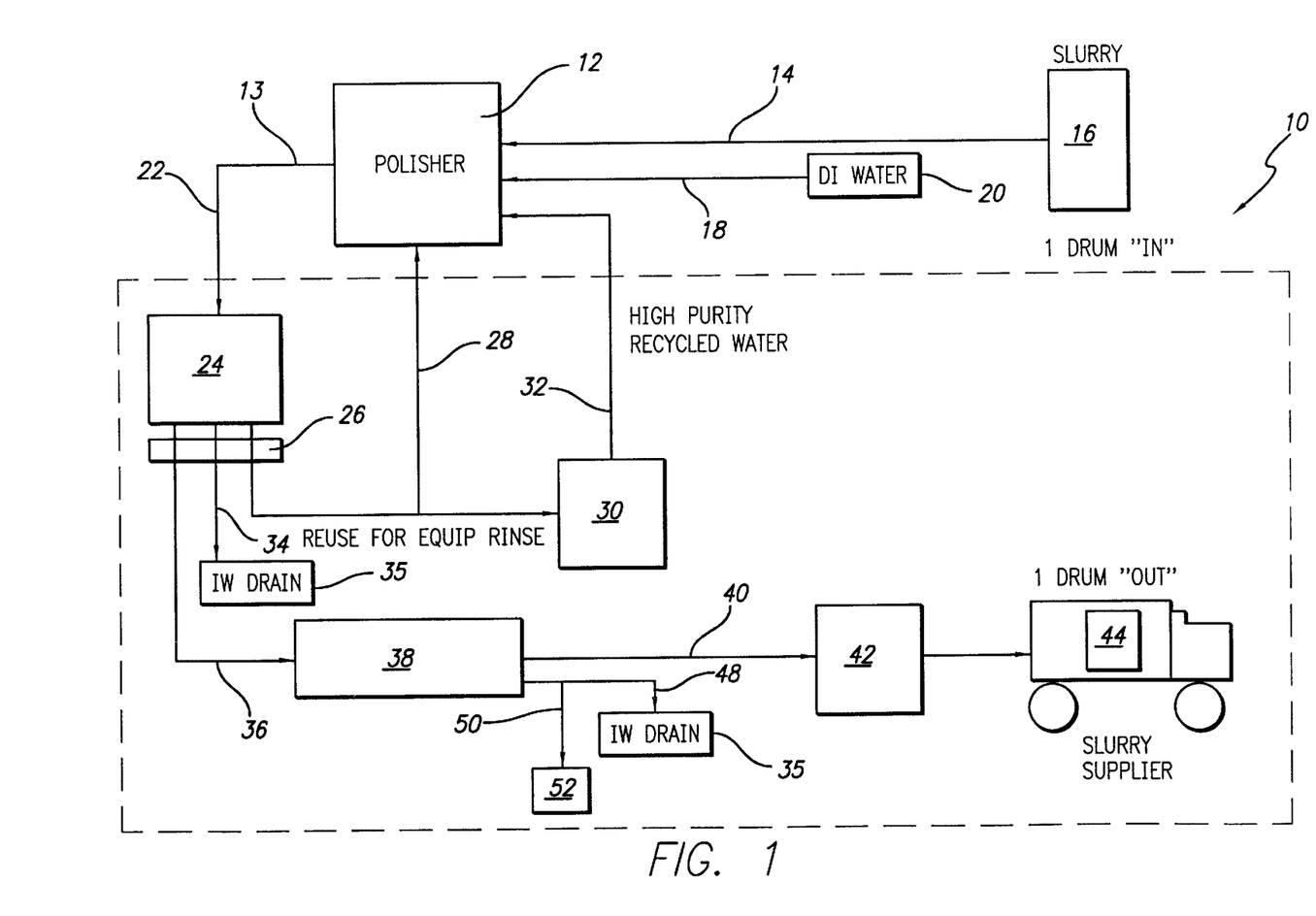
FIG. 1 is a schematic diagram of the method and apparatus of a first embodiment of the invention for recovering liquid and slurry abrasives that have been used from chemical mechanical planarization of semiconductor wafers.

As is illustrated in the drawings, the invention is accordingly embodied in a method and apparatus 10 for the separation and recovery of clear liquid from an aqueous waste stream that may contain abrasive materials, such as slurry abrasives used for polishing semiconductor wafers, and for the removal of the solids from the aqueous waste stream. Referring to FIG. 1, in a first presently preferred embodiment, a polishing tool 12 for polishing semiconductor wafers typically has an outlet 13, and receives the aqueous chemical mechanical slurry principally via line 14 from a source of the slurry 16, such as one or more drums or tanks containing one or more components of the chemical mechanical slurry. Deionized water (DI) can also be received by the polisher via line 18 from a source of deionized water 20, such as one or more drums or tanks, or a water deioinization apparatus. The raw waste stream, including the aqueous slurry containing abrasive particles and materials removed from planarization of semiconductor materials, is conducted from the polishing tool outlet via line 22 to a solids detection apparatus 24 for detecting the concentration of abrasive solids in the aqueous waste stream. The solids detection apparatus is typically located in close proximity to the polishing tool. When the solids detection apparatus indicates that the abrasive solids concentration is below a desired threshold, the entire effluent stream is diverted by a valve 26 via line 28 for reuse in non-critical rinsing applications in the polishing tool, or to an ion exchanger 30 for ion exchange treatment of the effluent stream prior to conducting the effluent stream via line 32 to the polishing tool for reuse, or in other process applications. When solids detection apparatus indicates that the abrasive solids concentration is above the desired threshold, the entire effluent stream, including the aqueous slurry containing abrasive particles and materials removed from planarization of semiconductor materials, is diverted via line 34 by the valve 26 to the industrial waste treatment system or drain 35 for disposal, or via line 36 to a concentrator apparatus 38 which further separates the clear liquid component from the abrasive solids and concentrates the abrasive solids for disposal. The concentrated abrasive solids and materials removed from planarization of semiconductor materials are diverted via line 40 to an apparatus 42 for filling one of several waste collection containers or drums 44 which, when filled, are removed for off-site processing, such as by a slurry supplier, for recycling. The clear liquid from the concentrator apparatus is returned via line 48 to the industrial waste treatment system or drain 35 for disposal, or via line 50 to a facility reverse osmosis/deionization process 52 for recycling.

Figure 2:
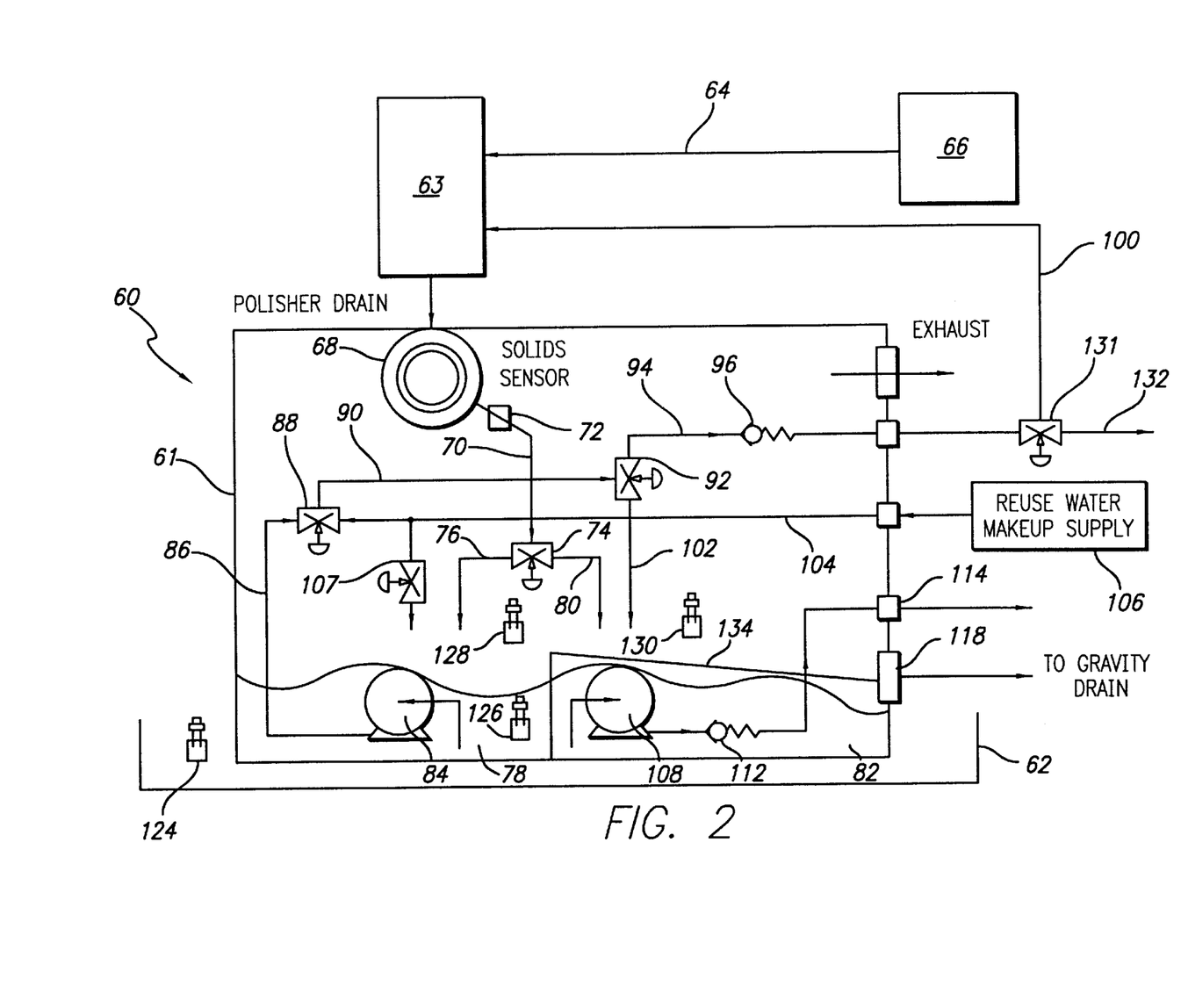
FIG. 2 is a schematic diagram of the apparatus of a first embodiment for detecting solids concentration in the effluent stream and diverting the clear liquid stream to the interface apparatus and back to the polisher.

Referring to FIG. 2, in a first presently preferred embodiment, an apparatus 60 according to the invention for the separation and recovery of clear liquid from an aqueous waste stream that may contain abrasive materials, such as slurry abrasives used for polishing semiconductor wafers, and for the removal of the solids from the aqueous waste stream includes a housing 61 disposed over a drip pan 62. A polishing tool 63 receives aqueous chemical mechanical slurry via line 64 from a source of the slurry 66, such as one or more drums or tanks containing one or more components of the chemical mechanical slurry. The raw waste stream, including the aqueous slurry containing abrasive particles and materials removed from planarization of semiconductor materials, is conducted from the polishing tool outlet 68 via line 70 to a solids detection apparatus 72 for detecting the concentration of abrasive solids and other materials in the aqueous waste stream. The solids detection apparatus receives raw aqueous effluent, possibly containing an aqueous slurry of abrasive particles, where the incoming flow and effluent conductivity and temperature of the effluent are typically also measured. If the solids detection apparatus indicates that the incoming effluent stream contains solids under a desired threshold, the entire effluent stream is diverted by a diverter valve 74 via line 76 to one or several reuse water drain sumps or collection tanks 78. Otherwise, the entire effluent stream containing abrasive solids is diverted by the diverter valve via line 80 to one or several concentrate water drain sumps or collection tanks 82.

Clear liquid is drawn from the one or several reuse water collection tanks by pump 84, and is transferred through line 86 through a deionized water by-pass valve 88, and from there via line 90 through a common valve 92 and via line 94 and check valve 96 through a skirt rinse/pressure drain 98 to return to the polishing tool via line 100 as non-process equipment rinse water. Alternatively, the reuse water can be diverted from the skirt rinse/pressure drain 98 to an ion exchanger (not shown) which produces high purity water for reuse via line 100 at the polisher as process water. When the supply in the one or several reuse water collection tanks is sufficient to meet the demand of the polisher, the excess recyclable water can be diverted by the common valve 131 via line 132 to other non-process applications, or the excess recyclable water can be diverted by the common valve 92 via line 102 to the industrial waste treatment system through an overflow reuse bypass line 122 to an overflow drain 118. When adequate reclaimed water is not available from one or several reuse water collection tanks, additional rinse water can be obtained and introduced by switching the deionized water by-pass valve to receive deionized water from a deionized water supply 106.

Figure 3:
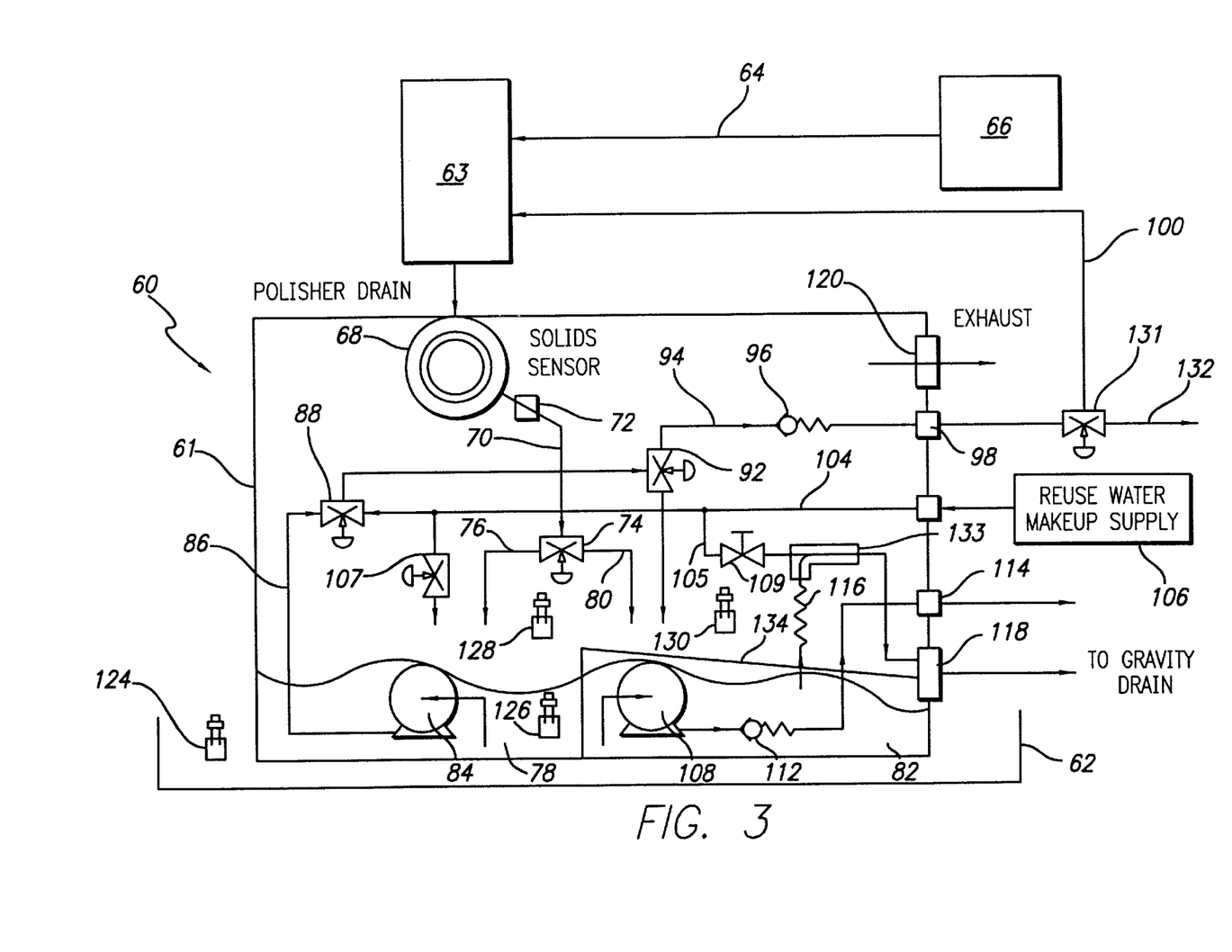
FIG. 3 is a schematic diagram of an alternate embodiment of the apparatus of FIG. 2.

Effluent containing abrasive solids and materials from polishing semiconductor wafers is drawn from the one or several concentrate water collection tanks by a pump 108, which transfers the effluent via line 110 through a check valve 112 to a pressurized concentrate water drain 114 leading to a solids concentrator apparatus for further processing of the effluent. Alternatively, as is illustrated in FIG. 3, any excess effluent in the one or several concentrate water collection tanks can be diverted through line 116 to the industrial waste treatment system via an aspirator 133 through an overflow drain 118. Reuse water makeup supply can be diverted from line 104 via line 105 by valve 109 to operate the aspirator 133.

The housing may also advantageously contain an exhaust 120, a leak detect sensor 124 in the drip pan, liquid level sensors 126, 128 in the one or several reuse water collection tanks, and a liquid level sensor 130 in the one or several concentrate water collection tanks.

Figure 4:
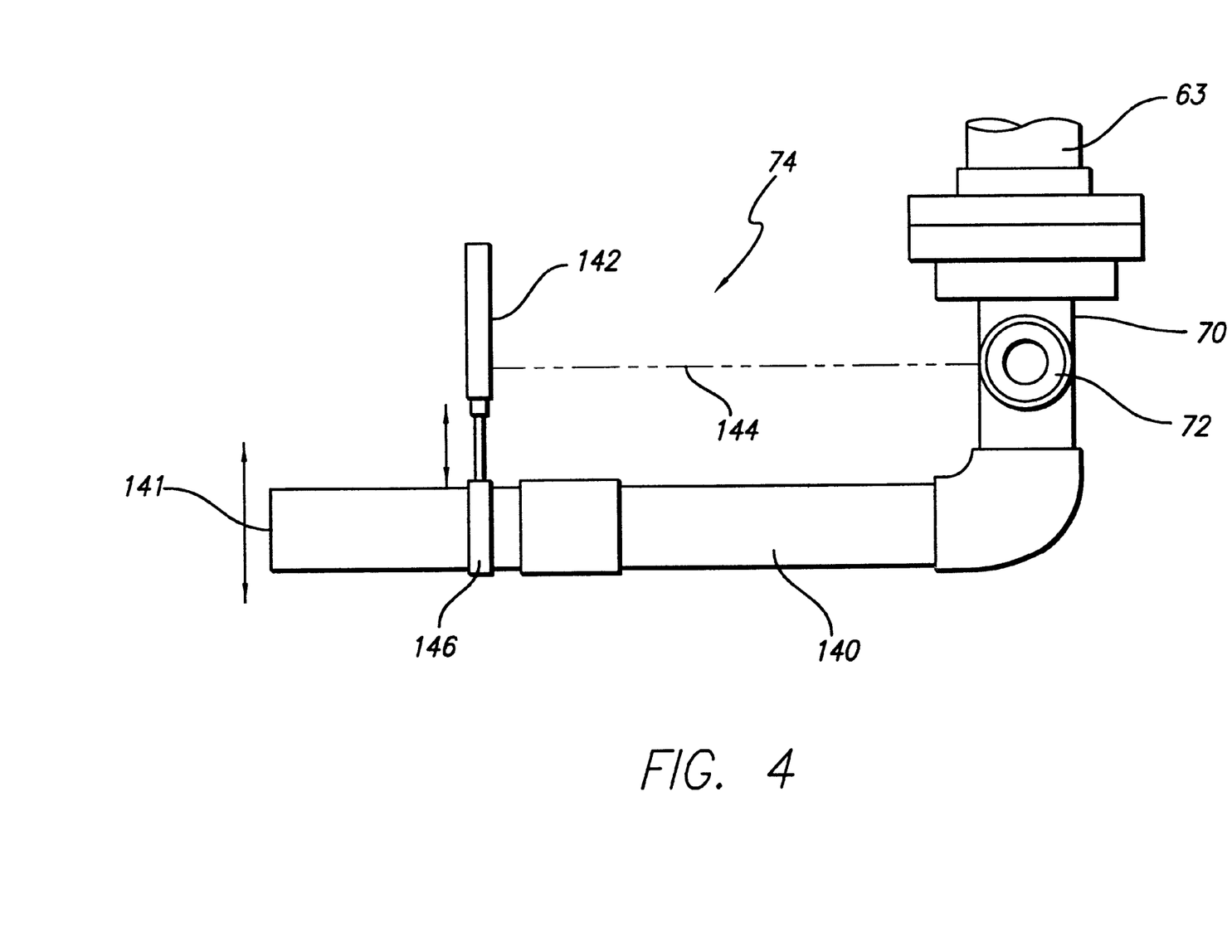
FIG. 4 is a schematic diagram of a first preferred diverter valve for diverting clear liquid from a slurry abrasive waste stream and thus concentrating said waste stream to maximize the recovery of clear liquid.

Referring to FIG. 4 illustrating a first preferred embodiment of the diverter valve 74 for diverting the clear liquid from the liquid containing abrasive solids in the waste stream, the diverter valve receives an aqueous solution from the outlet 63 of the polisher tool through the line 70. The aqueous solution passes through the solids detection apparatus 72, which can be a device to measure the conductivity, pH, density, turbidity, and the like, including other devices for detecting solids concentration, and combinations of such measurements. In a presently preferred embodiment, the solids detection apparatus is a sensor which detects solids concentration using light scattering turbidity measurement combined with conductivity and temperature. In the embodiment of FIG. 4, the diverter valve comprises a displaceable conduit connected to the line 70, such as a flexible hose 140 having an outlet 141 that can be moved by a piston cylinder 142 connected to the solids detection apparatus via a line 144, and actuatable between first and second positions by the solids detection apparatus, which is connected to the flexible hose by a collar 146. While the solids concentration is above a desired threshold, the solids detection apparatus causes the piston cylinder to move to its first position, directing the flexible hose outlet so as to allow the effluent to flow, typically into a trough (not shown), and on into the one or several concentrate water collection tanks 82. While the solids concentration is below a desired threshold, solids detection apparatus activates the piston cylinder to move to the second position, in which the flexible hose diverts the clear liquid of the effluent to the one or several reuse water collection tanks 78.

Figure 5:
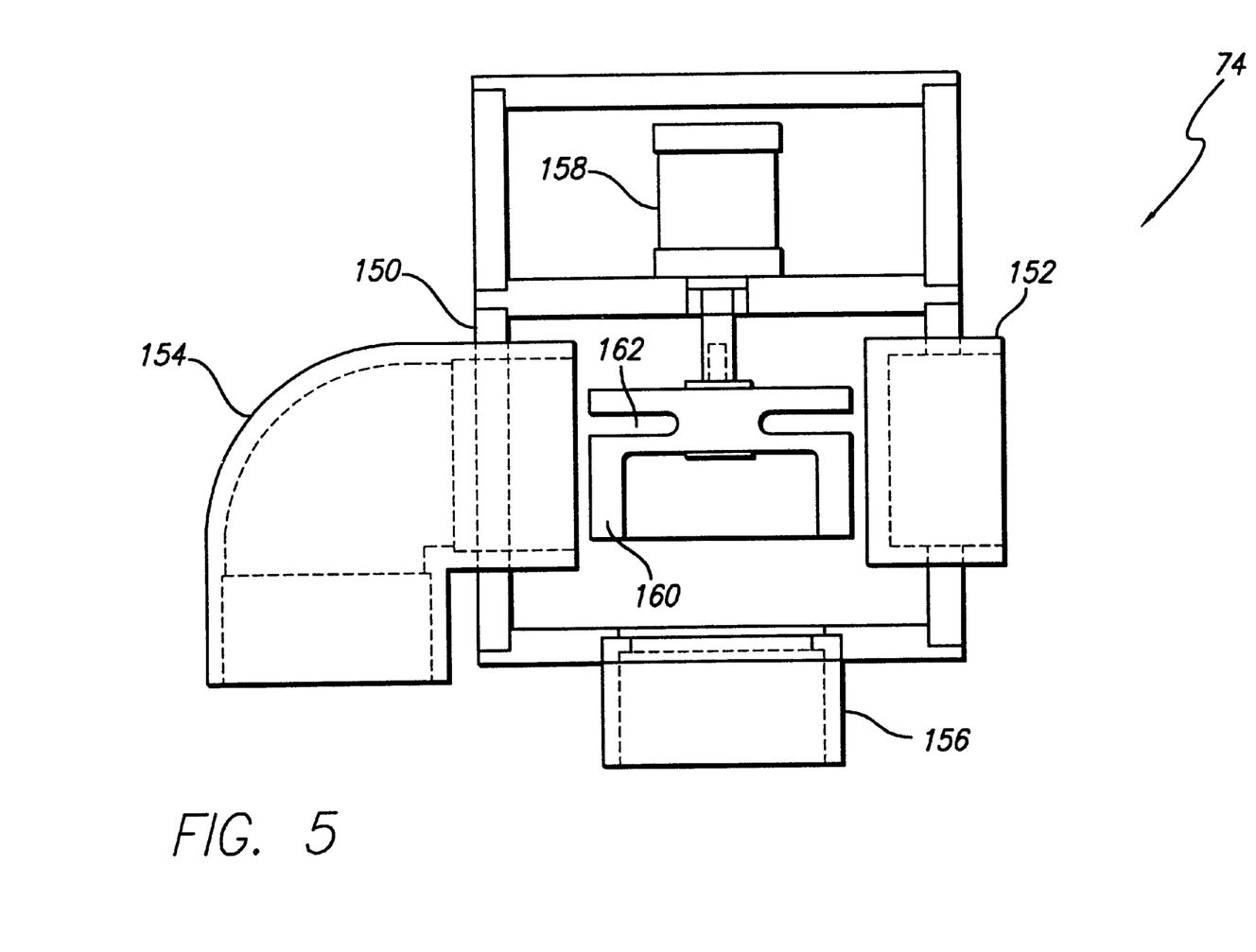
FIG. 5 is a schematic diagram of a second preferred diverter valve.

In another presently preferred embodiment, illustrated in FIG. 5, the diverter valve 74 can comprise a valve housing 150 having an inlet 152, a first outlet 154 for diverting flow to the one or several reuse water collection tanks, and a second outlet 156 for diverting flow to the one or several concentrate water collection tanks. A solenoid 158 connected for control by the solids detection apparatus is connected to a valve piston 160 movable between first and second positions, and may have a groove 162 to reduce the impact of actuation.

Figure 6:
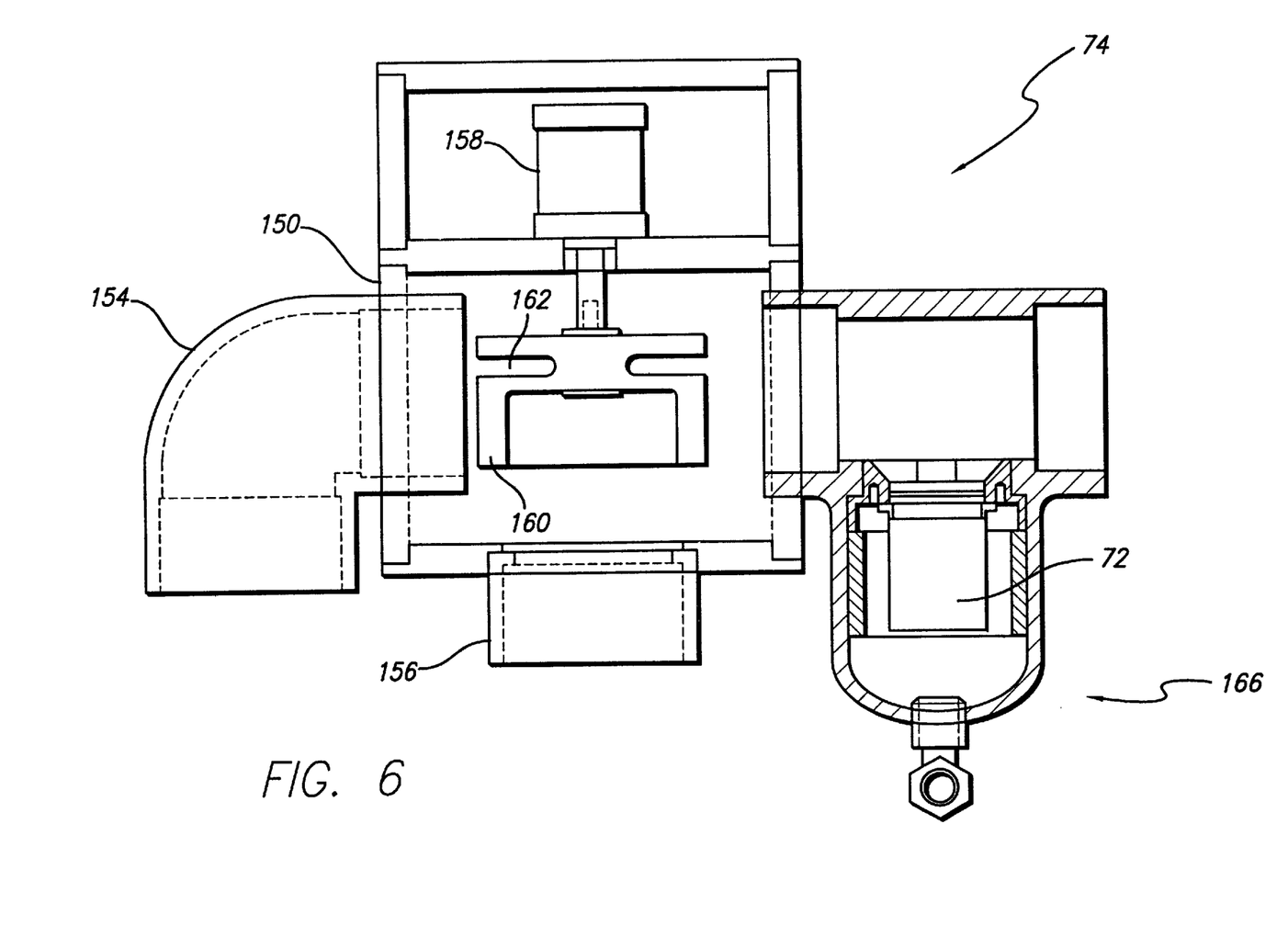
FIG. 6 is a schematic diagram of a modification of the second preferred diverter valve.

As is illustrated in FIG. 6, in a modification of the diverter valve 74 illustrated in FIG. 5, the diverter valve can include an integrated solids detection device located in the housing 166.

Figure 7:
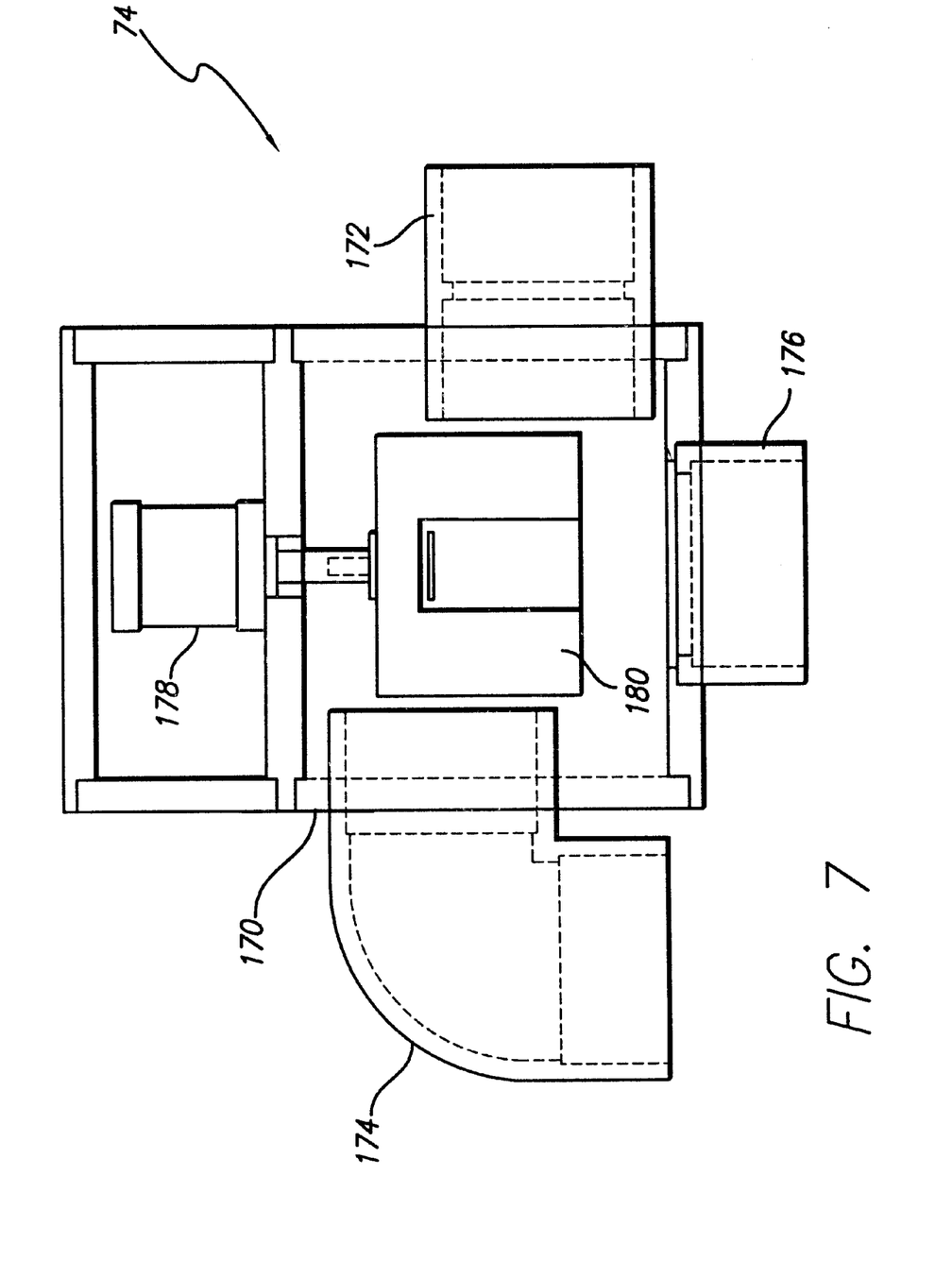
FIG. 7 is a schematic diagram of a third preferred diverter valve.

In another presently preferred embodiment, illustrated in FIG. 7, the diverter valve 74 can comprise a valve housing 170 having an inlet 172, a first outlet 174 for diverting flow to the one or several reuse water collection tanks, and a second outlet 176 for diverting flow to the one or several concentrate water collection tanks. A solenoid 178 connected for control by the solids detection apparatus is connected to a valve piston 180 movable between first and second positions, the valve piston blocking flow to the second outlet for diverting flow to the first outlet in the first valve piston position, and blocking flow to the first outlet for diverting flow to the second outlet in the second valve piston position.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. A method for the recovery of water from an aqueous slurry waste stream from chemical mechanical planarization of semiconductor wafers, the aqueous waste stream containing abrasive materials on an irregular basis, and for the removal of the abrasive materials from the aqueous slurry waste stream, comprising the steps of:

introducing an effluent stream of the aqueous slurry waste stream into a particle detection device for detection of a solids concentration of abrasive particles in the aqueous slurry waste stream; and diverting the entire effluent stream as collected water to at least one reuse water collection tank when the solids concentration is below a desired threshold, and diverting the entire effluent stream as concentrate water to a concentrate water collection tank when the solids concentration is greater than or equal to the desired threshold.

2. The method of claim 1 further comprising the step of pumping the collected water from said at least one reuse water collection tank for reuse.

3. The method of claim 2, further comprising the step of purifying the collected water by ion exchange.

4. The method of claim 1, further comprising the step of pumping the concentrate water to a concentration apparatus for concentrating the aqueous slurry waste stream.

5. The method of claim 1, wherein the particle detection device measures conductivity of the aqueous slurry waste stream, and further comprising the step of measuring conductivity of the aqueous slurry waste stream to determine the solids concentration prior to the step of diverting the entire effluent stream.

6. The method of claim 1, wherein the particle detection device measures temperature of the aqueous slurry waste stream, and further comprising the step of measuring temperature of the aqueous slurry waste stream to determine the solids concentration prior to the step of diverting the entire effluent stream.

7. The method of claim 1, wherein the particle detection device measures turbidity of the aqueous slurry waste stream, and further comprising the step of measuring turbidity of the aqueous slurry waste stream to determine the solids concentration prior to the step of diverting the entire effluent stream.

8. The method of claim 1, wherein the particle detection device measures pH of the aqueous slurry waste stream, and further comprising the step of measuring pH of the aqueous slurry waste stream to determine the solids concentration prior to the step of diverting the entire effluent stream.

9. A method for the recovery of water from an aqueous slurry waste stream from chemical mechanical planarization of semiconductor wafers, the aqueous slurry waste stream containing abrasive materials on an irregular basis, comprising the steps of:

introducing an aqueous slurry waste stream into a solids detection device;

determining the solids concentration in the aqueous slurry waste stream in the solids detection device;

diverting the entire aqueous slurry waste stream for reuse when the solids concentrations is below a desired threshold for recovery of water from the aqueous slurry waste stream; and diverting the entire aqueous slurry waste stream as a waste water stream when the solids concentration is greater than or equal to the desired threshold.

10. The method of claim 9, wherein the solids detection device measures conductivity of the aqueous slurry waste stream, and the step of determining the solids concentration in the aqueous slurry waste stream comprises measuring conductivity of the aqueous slurry waste stream to determine the solids concentration.

11. The method of claim 9, wherein the solids detection device measures temperature of the aqueous slurry waste stream, and the step of determining the solids concentration in the aqueous slurry waste stream comprises measuring temperature of the aqueous slurry waste stream to determine the solids concentration.

12. The method of claim wherein the solids detection device measures turbidity of the aqueous waste effluent stream, and the step of determining the solids concentration in the aqueous slurry waste stream comprises measuring turbidity of the aqueous slurry waste stream to determine the solids concentration.

13. The method of claim 9, wherein the solids detection device measures pH of the aqueous waste effluent stream, and the step of determining the solids concentration in the aqueous slurry waste stream comprises measuring pH of the aqueous slurry waste stream to determine the solids concentration.

* * * * *

UNITED STATES PATENT AND TRADEMARK OFFICE
CERTIFICATE OF CORRECTION

PATENT NO. : 6,482,325 B1
DATED : November 19, 2002
INVENTOR(S) : Gary L. Corlett et al.

It is certified that error appears in the above-identified patent and that said Letters Patent is hereby corrected as shown below:

<u>Column 10,</u>
Line 3, after "claim", add -- 9 --.

Signed and Sealed this

Eighteenth Day of March, 2003

JAMES E. ROGAN
*Director of the United States Patent and Trademark Office*